(12) United States Patent
Allemand et al.

(10) Patent No.: US 8,883,125 B2
(45) Date of Patent: Nov. 11, 2014

(54) COSMETIC COMPOSITION COMPRISING A CUCURBIC ACID COMPOUND AND A BLEND OF SULFONIC AND ACRYLIC POLYMERS

(75) Inventors: Sophie Allemand, Paris (FR); Marie Devie, Antony (FR); Florence Levy, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/009,247

(22) PCT Filed: Apr. 5, 2012

(86) PCT No.: PCT/FR2012/050753
§ 371 (c)(1),
(2), (4) Date: Nov. 4, 2013

(87) PCT Pub. No.: WO2012/143645
PCT Pub. Date: Oct. 26, 2012

(65) Prior Publication Data
US 2014/0050679 A1     Feb. 20, 2014

Related U.S. Application Data

(60) Provisional application No. 61/473,901, filed on Apr. 11, 2011, provisional application No. 61/473,904, filed on Apr. 11, 2011.

(30) Foreign Application Priority Data

Apr. 5, 2011   (FR) ........................................ 1152903
Apr. 5, 2011   (FR) ........................................ 1152904

(51) Int. Cl.
| | | |
|---|---|---|
| *A61K 8/00* | (2006.01) |
| *A01N 37/08* | (2006.01) |
| *A61K 8/365* | (2006.01) |
| *A61K 8/81* | (2006.01) |
| *A61Q 19/00* | (2006.01) |
| *A61K 8/60* | (2006.01) |
| *A61K 8/06* | (2006.01) |

(52) U.S. Cl.
CPC ........... *A61K 8/8147* (2013.01); *A61K 2800/52* (2013.01); *A61K 8/365* (2013.01); *A61Q 19/00* (2013.01); *A61K 2800/594* (2013.01); *A61K 8/8158* (2013.01); *A61K 8/604* (2013.01); *A61K 8/062* (2013.01)
USPC ............................................ 424/59; 514/573

(58) Field of Classification Search
None
See application file for complete search history.

(56) References Cited

U.S. PATENT DOCUMENTS

2006/0134234 A1 *   6/2006   Fonolla Moreno et al. .. 424/729

FOREIGN PATENT DOCUMENTS

EP        1 759 688        *   7/2007

OTHER PUBLICATIONS

English Machine Translation for Compain, EP 1 759 688; publication date Jul. 3, 2007; retreived from the internet on Jul. 21, 2014.*

* cited by examiner

*Primary Examiner* — Johann R Richter
*Assistant Examiner* — Katherine Peebles
(74) *Attorney, Agent, or Firm* — Novak Druce Connolly Bove + Quigg LLP

(57) ABSTRACT

The invention relates to a cosmetic composition comprising, in a physiologically acceptable aqueous medium, a cucurbic acid compound of formula (I)

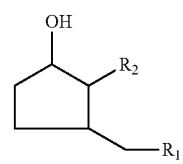

(I)

in which $R_1$ represents a radical $COOR_3$, $R_3$ denoting a hydrogen atom or a $C_1$-$C_4$ alkyl radical, optionally substituted with one or more hydroxyl groups;
$R_2$ represents a hydrocarbon-based radical containing from 1 to 18 carbon atoms;
a homopolymer of a monomer comprising a sulfonic group; and a crosslinked acrylic acid homopolymer.
Use for caring for and making up keratin materials.

20 Claims, No Drawings

COSMETIC COMPOSITION COMPRISING A CUCURBIC ACID COMPOUND AND A BLEND OF SULFONIC AND ACRYLIC POLYMERS

CROSS-REFERENCE TO RELATED APPLICATIONS

This application is a National Stage of PCT International Application No. PCT/FR2012/050753, filed on Apr. 5, 2012, and claims priority of French Patent Application Nos. 1152903, filed on Apr. 5, 2001, 1152904, filed on Apr. 5, 2011 and Provisional Patent Application Nos. 61/473,901, filed on Apr. 11, 2011 and 61/473,904, filed on Apr. 11, 2011. The disclosures of the aforementioned applications are incorporated herein in their entirety by reference.

The present invention relates to compositions, in particular cosmetic compositions, comprising a cucurbic acid compound and a blend of sulfonic and acrylic polymers, and also to the use of these compositions in a process for treating human keratin materials.

More particularly, the compositions of the invention are intended for caring for and/or making up keratin materials.

For the purposes of the invention, the term "keratin materials" is intended to denote, for example, the skin, the mucous membranes, the lips, the scalp, the eyelashes, the eyebrows and the hair.

Patent application EP-A-1 333 021 discloses hydrogenated cucurbic acid compounds such as 3-hydroxy-2-pentylcyclopentaneacetic acid for promoting desquamation of the skin and stimulating epidermal renewal, combating the signs of aging of the skin, improving the radiance of the complexion and/or making facial skin smooth. In patent application FR-A-62921255, these compounds are also described for their use as depigmenting agents.

However, the introduction of the hydrogenated cucurbic acid compounds previously mentioned into an aqueous cosmetic formulation can result in a not insignificant decrease in viscosity, thus inducing substantial fluidization of the composition and consequently destabilization of the composition.

A composition which is too fluid is difficult to apply to keratin materials. Such a composition runs on keratin materials, in particular on the skin, onto which it is applied. Its application to the keratin materials that it is desired to treat lacks precision and therefore makes it relatively unattractive to use.

In addition, the presence of a hydrogenated cucurbic acid compound is found to affect the thickening capacity of certain conventional gelling agents. In particular, this compound destabilizes aqueous gels of 2-acrylamido-2-methylpropanesulfonic acid homopolymer owing to a substantial drop in viscosity.

Thus, there is a need to have cosmetic compositions comprising a cucurbic acid compound and a homopolymer of a monomer comprising a sulfonic group (in particular a 2-acrylamido-2-methylpropanesulfonic acid homopolymer) which does not spontaneously exhibit substantial fluidization (no substantial drop in viscosity).

Surprisingly, the inventors have observed that the addition of a crosslinked acrylic acid homopolymer as described hereinafter makes it possible to obtain a composition of which the viscosity remains stable, without substantial fluidization. In particular, the composition exhibits good stability over time, in particular after storage for 2 months at ambient temperature (25° C.).

The object of the present invention is, precisely, to satisfy these needs.

In addition, the composition according to the invention, when it is applied to keratin materials, and in particular to the skin, does not exhibit any tacky sensation.

More specifically, the present invention relates to a composition comprising, in a physiologically acceptable medium containing an aqueous medium, at least one cucurbic acid compound of formula (I), a homopolymer of a monomer comprising a sulfonic group, and a crosslinked acrylic acid homopolymer, as described hereinafter.

The composition according to the invention is in particular a cosmetic composition.

The present invention also relates to a non-therapeutic treatment process for caring for or making up keratin materials, comprising the application to said keratin materials of a composition in accordance with the invention. Advantageously, such a process is intended for caring for or making up the skin.

The cucurbic acid-based compound is a compound chosen from those corresponding to formula (I) below:

in which:
$R_1$ represents a radical $COOR_3$, $R_3$ denoting a hydrogen atom or a $C_1$-$C_4$ alkyl radical, optionally substituted with one or more hydroxyl groups;
$R_2$ represents a saturated or unsaturated linear hydrocarbon-based radical containing from 1 to 18 carbon atoms or a saturated or unsaturated branched or cyclic hydrocarbon-based radical containing from 3 to 18 carbon atoms;
and also the optical isomers thereof, and corresponding salts.

Preferably, $R_1$ denotes a radical chosen from —COOH, —COOMe, —COO—CH$_2$—CH$_3$, —COO—CH$_2$—CH(OH)—CH$_2$OH, —COOCH$_2$—CH$_2$—CH$_2$OH, —COOCH$_2$—CH(OH)—CH$_3$. Preferentially, $R_1$ denotes a radical —COOH.

Preferentially, $R_2$ denotes a saturated or unsaturated linear hydrocarbon-based radical preferably containing from 2 to 7 carbon atoms. In particular, $R_2$ may be a pentyl, pentenyl, hexyl or heptyl radical.

According to one embodiment, the compound of formula (I) is chosen from 3-hydroxy-2-[(2Z)-2-pentenyl]cyclopentaneacetic acid and 3-hydroxy-2-pentylcyclopentaneacetic acid. Preferably, compound (I) is 3-hydroxy-2-pentylcyclopentaneacetic acid; this compound may in particular be in the sodium salt form.

The salts of the compounds that may be used according to the invention are chosen in particular from salts of alkali metals, for example sodium or potassium; salts of alkaline-earth metals, for example calcium, magnesium or strontium; metal salts, for example zinc, aluminum, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts. Salts chosen from sodium, potassium, magnesium, strontium, copper, manganese and zinc salts are preferably used. The sodium salt is preferentially used.

The compound of formula (I) defined previously may be present in the composition according to the invention in a content ranging from 1% to 10% by weight, and preferably from 1.5% to 5% by weight, relative to the total weight of the composition.

The composition according to the invention comprises a homopolymer of a monomer comprising a sulfonic group.

The composition according to the invention also comprises a polymer comprising at least one monomer comprising a sulfonic group. The presence of this polymer makes it possible to obtain a composition that has good stability properties.

The polymers comprising at least one monomer comprising a sulfonic group that are used in the composition of the invention are water-soluble or water-dispersible or water-swellable. The polymers used in accordance with the invention are homopolymers that may be obtained from at least one ethylenically unsaturated monomer comprising a sulfonic group, which may be in free form or partially or totally neutralized form.

Preferentially, the polymers in accordance with the invention may be partially or totally neutralized with an inorganic base (sodium hydroxide, potassium hydroxide or aqueous ammonia) or an organic base such as monoethanolamine, diethanolamine or triethanolamine, an aminomethylpropanediol, N-methylglucamine, basic amino acids, for instance arginine and lysine, and mixtures of these compounds. They are generally neutralized. In the present invention, the term "neutralized" is intended to mean polymers that are totally or virtually totally neutralized, i.e. at least 90% neutralized.

The polymers used in the composition of the invention generally have a number-average molecular weight ranging from 1000 to 20 000 000 g/mol, preferably ranging from 20 000 to 5 000 000 g/mol and even more preferentially from 100 000 to 1 500 000 g/mol.

These polymers according to the invention may be crosslinked or noncrosslinked.

The monomers comprising a sulfonic group of the polymer used in the composition of the invention are in particular chosen from vinylsulfonic acid, styrenesulfonic acid, (meth)acrylamido($C_1$-$C_{22}$)alkylsulfonic acids, N—($C_1$-$C_{22}$)alkyl (meth)acrylamido($C_1$-$C_{22}$)alkylsulfonic acids such as undecylacrylamidomethanesulfonic acid, and also partially or totally neutralized forms thereof, and mixtures thereof.

According to one preferred embodiment of the invention, the monomers comprising a sulfonic group are chosen from (meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, 2-methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid and 2-acrylamido-2,6-dimethyl-3-heptanesulfonic acid, and also partially or totally neutralized forms thereof, and mixtures thereof.

More particularly, use is made of 2-acrylamido-2-methylpropanesulfonic acid (AMPS), and also partially or totally neutralized forms thereof.

When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl(meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The homopolymer of monomers comprising a sulfonic group may be crosslinked with one or more crosslinking agents.

These homopolymers are generally crosslinked and neutralized, and they may be obtained according to the preparation process comprising the following steps:
(a) the monomer such as 2-acrylamido-2-methylpropanesulfonic acid in free form is dispersed or dissolved in a solution of tert-butanol or of water and tert-butanol;
(b) the monomer solution or dispersion obtained in (a) is neutralized with one or more inorganic or organic bases, preferably aqueous ammonia $NH_3$, in the amount making it possible to obtain a degree of neutralization of the sulfonic acid functions of the polymer ranging from 90% to 100%;
(c) the crosslinking monomer(s) are added to the solution or dispersion obtained in (b);
(d) a standard free-radical polymerization is performed in the presence of free-radical initiators at a temperature ranging from 10 to 150° C.; the polymer precipitates in the tert-butanol-based solution or dispersion.

The preferred AMPS homopolymers are generally characterized in that they comprise, randomly distributed:
a) from 90% to 99.9% by weight of units of general formula (II) below:

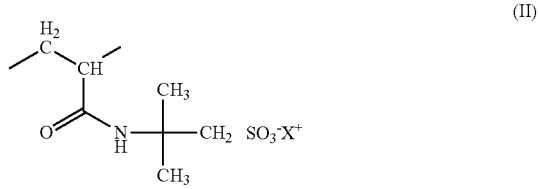

in which $X^+$ denotes a proton, an alkali metal cation, an alkaline-earth metal cation or the ammonium ion, not more than 10 mol % of the cations $X^+$ possibly being protons $H^+$;
b) from 0.01% to 10% by weight of crosslinking units originating from at least one monomer containing at least two olefinic double bonds; the weight proportions being defined relative to the total weight of the polymer.

The homopolymers according to the invention that are more particularly preferred comprise from 98% to 99.5% by weight of units of formula (II) and from 0.2% to 2% by weight of crosslinking units.

A polymer of this type that may in particular be mentioned is the crosslinked and neutralized 2-acrylamido-2-methylpropanesulfonic acid homopolymer sold by the company Clariant under the trade name Hostacerin® AMPS (CTFA name: ammonium polyacryldimethyltauramide).

The homopolymer of a monomer comprising a sulfonic group may be present in the composition according to the invention in an active material content ranging, for example, from 0.05% to 5% by weight, preferably ranging from 0.1% to 5% by weight, preferentially ranging from 0.1% to 2% by weight, relative to the total weight of the composition.

Advantageously, the cucurbic acid compound of formula (I) (referred to as A) and the homopolymer of a monomer comprising a sulfonic group (referred to as B), described previously, may be present in the composition according to the invention in an NB weight ratio ranging from 3 to 4.5.

The composition according to the invention contains a crosslinked acrylic acid homopolymer.

The homopolymer may be crosslinked with a crosslinking agent, in particular chosen from pentaerythritol allyl ether, sucrose allyl ether, or propylene allyl ether.

Such polymers have the INCI name: Carbomer

Use may, for example, be made of the polymers sold by the company Lubrizol under the names Carbopol 980 or 981, or Carbopol Ultrez 10, or by the company 3V under the name Synthalen K or Synthalen L or Synthalen M.

The acrylic acid homopolymer may be present in the composition according to the invention in an amount ranging from 0.01% to 5% by weight, and preferably from 0.1% to 3% by weight, relative to the total weight of the composition.

Advantageously, the cucurbic acid compound of formula (I) (referred to as A) and the acrylic acid homopolymer (referred to as C), described previously, may be present in the composition according to the invention in an NC weight ratio ranging from 2 to 20 and preferably from 4.5 to 5.5.

The viscosity of a composition of the invention may be measured via any method known to those skilled in the art, and in particular according to the following conventional method. Thus, the measurement can be carried out at 25° C. using a Rheomat 180 viscometer equipped with a spindle rotating at 200 rpm. Those skilled in the art may select the spindle for measuring the viscosity from the spindles M1, M2, M3 and M4 on the basis of their general knowledge, so as to be able to perform the measurement.

The composition according to the invention comprises a physiologically acceptable aqueous medium.

The term "physiologically acceptable medium" is intended to denote a medium that is compatible with human keratin materials and/or fibers, for instance, in a nonlimiting manner, the skin, the mucous membranes, the nails, the scalp and/or the hair.

This physiologically acceptable aqueous medium comprises an aqueous phase, optionally as a mixture, or not, with one or more organic solvents, such as a $C_1$-$C_8$ alcohol, in particular ethanol, isopropanol, tert-butanol, n-butanol, polyols such as glycerol, propylene glycol, butylene glycol, and polyol ethers.

A composition according to the invention may also comprise a fatty phase, which may comprise oils, gums and waxes normally used in the field of application under consideration.

Thus, according to one embodiment, a composition according to the invention may also comprise at least one fatty phase chosen from a fatty phase which is solid at ambient temperature (20-25° C.) and atmospheric pressure and/or a fatty phase which is liquid at ambient temperature (20-25° C.) and atmospheric pressure.

A liquid fatty phase suitable for implementing the invention may comprise a volatile oil, a non-volatile oil, and a mixture thereof. A volatile or non-volatile oil may be a hydrocarbon-based oil, in particular of animal or vegetable origin, a synthetic oil, a silicone oil, a fluoro oil or a mixture thereof.

A solid fatty phase suitable for implementing the invention may be chosen, for example, from pasty fatty substances and gums, and mixtures thereof.

As oils that can be used in the invention, mention may be made of mineral oils (liquid petroleum jelly), vegetable oils (liquid fraction of shea butter, sunflower oil), synthetic oils (Purcellin oil), silicone-based oils or waxes (cyclomethicone) and fluorinated oils (perfluoropolyethers). Fatty alcohols and fatty acids (stearic acid) may be added to these oils.

When a composition is an emulsion, the proportion of the fatty phase may range from 5% to 80% by weight and preferably from 5% to 50% by weight relative to the total weight of the composition. The oils, waxes, emulsifiers and co-emulsifiers used in the composition in emulsion form are chosen from those conventionally used in the cosmetics field.

One or more emulsifiers may be present in a composition of the invention in a proportion ranging from 0.3% to 30% by weight and in particular from 0.5% to 20% by weight relative to the total weight of the composition.

When the composition is in the form of an oil-in-water emulsion, it preferably comprises a surfactant of polyalkylglucoside type.

More specifically, the present invention also relates to a composition in the form of an oil-in-water emulsion, comprising a cucurbic acid compound of formula (I), a surfactant of alkylpolyglycoside type, a homopolymer of a monomer comprising a sulfonic group, and a crosslinked acrylic acid homopolymer, as described hereinafter.

The emulsions obtained are particularly stable. In particular, the composition exhibits good stability after storage for 2 months at 45° C.

In addition, the compositions according to the invention are pleasant to apply to keratin materials, in particular to the skin; it has a texture which fluidizes during spreading, going from a thickened fluid state to a liquid state. This application is carried out with no tacky or pilling sensation.

The composition according to the invention comprises at least one surfactant of alkylpolyglycoside type.

For the purposes of the present invention, the term "alkylpolyglycoside" is intended to mean an alkylmonosaccharide (degree of polymerization 1) or an alkylpolysaccharide (degree of polymerization greater than 1).

The alkylpolyglycosides may be used alone or in the form of mixtures of several alkylpolyglycosides. They generally correspond to the following structure:

$$R(O)(G)_x$$

in which the radical R is a linear or branched $C_{12}$-$C_{22}$ alkyl radical, G is a saccharide residue and x ranges from 1 to 5, preferably from 1.05 to 2.5 and more preferentially from 1.1 to 2.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch. More preferentially, the saccharide residue denotes glucose.

It should also be noted that each unit of the polysaccharide part of the alkylpolyglycoside may be in α or β isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

The surfactant of alkylpolyglycoside type may be present in a composition of the invention in a content ranging from 0.1% to 1.6% by weight, relative to the total weight of the composition, preferably ranging from 0.1% to 1.5% by weight and preferentially ranging from 0.1% to 1% by weight.

According to one particular mode of the invention, the composition according to the invention may also comprise at least one fatty alcohol, in particular a fatty alcohol containing from 10 to 30 carbon atoms.

As examples of fatty alcohols that may be used, mention may be made of linear or branched fatty alcohols, of synthetic origin or alternatively of natural origin, for instance alcohols originating from vegetable material (coconut, palm kernel, palm, etc.) or animal material (tallow, etc.).

Use is preferably made of a fatty alcohol comprising from 20 to 26 carbon atoms, preferably from 10 to 24 carbon atoms and more preferentially from 12 to 22 carbon atoms.

As particular examples of fatty alcohols that may be used in the context of the present invention, mention may in particular be made of lauryl alcohol, myristyl alcohol, cetyl alcohol, stearyl alcohol, isostearyl alcohol, palmityl alcohol, oleyl alcohol, cetearyl alcohol (mixture of cetyl alcohol and stearyl alcohol), behenyl alcohol, erucyl alcohol and arachidyl alcohol, and mixtures thereof.

In addition, it is particularly advantageous, according to the present invention, to use together a fatty alcohol and an alkylpolyglycoside of which the alkyl part is identical to that of the selected fatty alcohol.

Fatty alcohol/alkylpolyglycoside emulsifying mixtures as defined are described in particular in patent applications WO 92/06778, WO 95/13863 and WO 98/47610.

Among the fatty alcohol/alkylpolyglycoside mixtures that are particularly preferred, mention may be made of the products sold by the company SEPPIC under the name Montanov®, such as the following mixtures:

cetylstearyl alcohol/cocoyl glucoside—Montanov 82®,
arachidyl alcohol and behenyl alcohol/arachidyl glucoside—Montanov 802®,
myristyl alcohol/myristyl glucoside—Montanov 14®,
cetylstearyl alcohol/cetylstearyl glucoside—Montanov 68®,
$C_{14}$-$C_{22}$ alcohol/$C_{12}$-$C_{20}$ alkyl glucoside—Montanov L®,
cocoyl alcohol/cocoyl glucoside—Montanov S®, and
isostearyl alcohol/isostearyl glucoside—Montanov WO 18®.

According to one particular embodiment, the alkylpolyglycoside used in a composition according to the invention is $C_{12}$-$C_{20}$ glucoside. It is advantageously used as a mixture with a $C_{14}$-$C_{22}$ alcohol.

According to one particular embodiment of the invention, use is thus made of the $C_{14}$-$C_{22}$ alcohol/$C_{12}$-$C_{20}$ alkylglucoside mixture, such as the product sold by the company SEPPIC under the name Montanov 68®, consisting of approximately 20% of $C_{12}$-$C_{20}$ alkylglucoside and of approximately 80% of $C_{14}$-$C_{22}$ alcohol.

The fatty alcohol may be present in a composition of the invention in a content ranging from 0.4% to 8% by weight, relative to the total weight of the composition, preferably ranging from 0.1% to 1% by weight and preferentially ranging from 0.6% to 2% by weight.

The fatty alcohol/alkylpolyglycoside mixture may be present in a composition of the invention in a content ranging from 0.5% to 8% by weight, relative to the total weight of the composition, preferably ranging from 0.6% to 5% by weight and more preferentially ranging from 0.8% to 2.5% by weight.

According to one particular embodiment, a composition in accordance with the invention may comprise said compound of formula (I) and said alkylpolyglycoside in a compound (I)/alkylpolyglycoside weight ratio ranging from 15 to 25, preferably ranging from 17 to 23 and preferentially ranging from 18 to 22.

In the particular case where the alkylpolyglycoside is used in combination with at least one fatty alcohol as previously described, the composition of the invention may then advantageously comprise said mixture of alkylpolyglycoside and of fatty alcohol and said compound of formula (I) in a compound (I)/(alkylpolyglycoside+fatty alcohol) weight ratio ranging from 3 to 5, preferably ranging from 3.4 to 4.6 and preferentially ranging from 3.6 to 4.4. Preferably, the viscosity of the emulsions comprising a alkylpolyglycoside can range from 0.086 Pa·s$^{-1}$ to 1.4 Pa·s$^{-1}$. Advantageously, this viscosity can range from 0.20 Pa·s$^{-1}$ to 1.1 Pa·s$^{-1}$.

Advantageously, the cucurbic acid compound of formula (I) (referred to as A) and the homopolymer of a monomer comprising a sulfonic group (referred to as B), described previously, may be present in the emulsions according to the invention comprising a surfactant of alkylpolyglycoside type in an NB weight ratio ranging from 3.5 to 6.5.

Preferably, this A/B weight ratio may range from 4 to 6. Preferentially, this NB weight ratio may range from 4.5 to 5.5.

Advantageously, the cucurbic acid compound of formula (I) (referred to as A) and the acrylic acid homopolymer (referred to as C), described previously, may be present in the emulsions according to the invention comprising a surfactant of alkylpolyglycoside type in an A/C weight ratio ranging from 8 to 12. Preferably, this NC weight ratio may range from 9 to 11. Preferentially, this NC weight ratio may range from 9.5 to 10.5.

The composition may comprise water in a content ranging from 20% to 95% by weight, relative to the total weight of the composition, preferably ranging from 30% to 90% by weight and preferentially ranging from 40% to 70% by weight.

The water may be a floral water such as cornflower water and/or a mineral water such as Vittel water, Lucas water or La Roche Posay water and/or a spring water.

The composition may also comprise an organic solvent that is water-miscible at ambient temperature (25° C.), chosen in particular from monoalcohols containing from 2 to 6 carbon atoms, such as ethanol or isopropanol;
polyols in particular containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol;
glycol ethers (in particular containing from 3 to 16 carbon atoms) such as mono-, di- or tripropylene glycol ($C_1$-$C_4$)alkyl ethers, and mono-, di- or triethylene glycol ($C_1$-$C_4$)alkyl ethers;
and mixtures thereof.

The composition according to the invention may comprise an organic solvent that is miscible with water at ambient temperature, in particular a polyol, in a content ranging from 1% to 20% by weight and preferably ranging from 3% to 15% by weight relative to the total weight of the composition.

Advantageously, the composition according to the invention has a pH ranging from 5.5 to 7.5.

The emulsion according to the invention also comprises an oily phase.

Mention may be made, as oils which can be used in the composition of the invention, for example, of:
hydrocarbon oils of vegetable origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by Stearineries Dubois or those sold under the names Miglyol 810, 812 and 818 by Dynamit Nobel, jojoba oil and shea butter oil;

synthetic esters and ethers, in particular of fatty acids, for instance the oils of formulae $R_1COOR_2$ and $R_1OR_2$ in which $R_1$ represents a fatty acid residue containing from 8 to 29 carbon atoms and $R_2$ represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of inorganic or synthetic origin, such as volatile or non-volatile liquid paraffins, and derivatives thereof, petroleum jelly, polydecenes, and hydrogenated polyisobutene such as Parleam oil;

fatty alcohols having from 8 to 26 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, for instance those described in document JP-A-2-295 912;

silicone oils, such as volatile or non-volatile polymethylsiloxanes (PDMSs) with a linear or cyclic silicone chain, which are liquid or pasty at ambient temperature, in particular cyclopolydimethylsiloxanes (cyclomethicones), such as cyclohexasiloxane; polydimethylsiloxanes comprising alkyl, alkoxy or phenyl groups, which are pendent or at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates and polymethylphenylsiloxanes;

mixtures thereof.

In the list of the abovementioned oils, the term "hydrocarbon-based oil" is intended to mean any oil predominantly comprising carbon and hydrogen atoms, and optionally ester, ether, fluoro, carboxylic acid and/or alcohol groups.

The oil may be present in the composition according to the invention in a content ranging from 0.5% to 20% by weight, relative to the total weight of the composition, and preferably ranging from 1% to 15% by weight.

The oily phase of the emulsion may comprise other fatty substances, such as, for example, fatty acids containing from 8 to 30 carbon atoms, for instance stearic acid, lauric acid, palmitic acid and oleic acid; waxes, for instance lanolin wax, beeswax, carnauba wax or candelilla wax, paraffin wax, lignite wax or microcrystalline waxes, ceresin or ozokerite, and synthetic waxes, for instance polyethylene waxes and Fischer-Tropsch waxes; silicone resins such as trifluoromethyl-$C_{1-4}$-alkyl dimethicone and trifluoropropyl dimethicone; and silicone elastomers, for instance the products sold under the name KSG by the company Shin-Etsu, under the name Trefil, BY29 or EPSX by the company Dow Corning, or under the name Gransil by the company Grant Industries.

These fatty substances can be chosen in a manner varied by those skilled in the art in order to prepare a composition having the desired properties, for example of consistency or texture.

The composition according to the invention may also contain cosmetic adjuvants in particular chosen from emulsifiers, gelling agents, oils, waxes, preservatives, antioxidants, water, fragrances, fillers, UV screens, pigments, fibers, chelating agents, odor absorbers and colorants.

The amounts of these various adjuvants are those conventionally used in the cosmetics field, and may range, for example, from 0.01% to 30% of the total weight of the composition. In general, the amounts are adjusted as a function of the formulation prepared. Depending on their nature, these adjuvants may be introduced into the fatty phase, into the aqueous phase and/or into lipid spherules.

The composition according to the invention may be in the form of an aqueous or aqueous-alcoholic solution; a dispersion; a water-in-oil, oil-in-water or multiple emulsion; a suspension; microcapsules or microparticles; vesicular dispersions of ionic and/or nonionic type; or an aerosol composition also comprising a pressurized propellant. Preferentially, the composition according to the invention may be an oil-in-water or water-in-oil emulsion. More preferentially, the composition according to the invention is an oil-in-water emulsion.

When the composition comprises an oily phase, the latter may comprise a silicone elastomer. Examples of silicone elastomers are described in patent application WO-A-2009/080 958.

A composition according to the invention may also be in the form of a care product, an antisun or after-sun product, a daily photoprotective care product, a body product, a foundation to be applied to the face or the neck, a concealer product, a complexion corrector, a tinted cream or a makeup base for making up the face, or a body makeup composition.

A composition according to the invention may be used for the purposes of improving the general condition of the epidermis, in particular of the skin, and in particular for maintaining or restoring its physiological functions and/or its esthetic appearance.

Other characteristics and advantages of the invention will emerge more clearly from the examples that follow, which are given as nonlimiting illustrations. In the text hereinbelow or hereinabove, the proportions are given as weight percentages, unless otherwise indicated.

COMPARATIVE EXAMPLES 1 AND 2

An aqueous gel (ex 1) according to the invention containing the blend of sulfonic and acrylic polymers, and an aqueous gel not part of the invention (ex 2) which is similar but contains only the sulfonic polymer were prepared; each gel was prepared with or in the absence of the sodium salt of 3-hydroxy-2-pentylcyclopentaneacetic acid.

The viscosity of the aqueous gels obtained was then measured after 24 hours of storage at ambient temperature (viscosity measured at 25° C. using a Rheomat 180 viscometer with an M3 spindle after 10 minutes of rotation at 200 rpm).

The following results were obtained:

| | Example 1A | Example 1B (invention) |
|---|---|---|
| Sodium salt of 3-hydroxy-2-pentylcyclopentaneacetic acid at 30% in a water/dipropylene glycol mixture (70/30) | 0 | 6.6%, i.e. 2% AM |

-continued

|  | Example 1A | Example 1B (invention) |
|---|---|---|
| Polyacrylamidomethylpropanesulfonic acid partially neutralized with aqueous ammonia and highly crosslinked (Hostacerin AMPS ® from Clariant) | 0.6% AM | 0.6% AM |
| Crosslinked acrylic acid homopolymer (Synthalen K from 3V) | 0.4% | 0.4% |
| Water | qs 100% | qs 100% |
| Viscosity (Pa · s) | 4 | 0.15 |

|  | Example 2A | Example 2B CONTROL |
|---|---|---|
| Sodium salt of 3-hydroxy-2-pentylcyclopentaneacetic acid at 30% in a water/dipropylene glycol mixture (70/30) | 0 | 6.6%, i.e. 2% AM |
| Polyacrylamidomethylpropanesulfonic acid partially neutralized with aqueous ammonia and highly crosslinked (Hostacerin AMPS ® from Clariant) | 1% AM | 1% AM |
| Water | qs 100% | qs 100% |
| Viscosity (Pa · s) | 4 | 0.038 |

These tests show that the combination of sulfonic polymer (Hostacerin Amps) and crosslinked acrylic polymer (Carbomer such as Synthalen K) in the presence of the sodium salt of 3-hydroxy-2-pentylcyclopentaneacetic acid exhibits a small variation in viscosity.

Thus, the presence of the blend of the acrylic polymer makes it possible to avoid a very substantial drop in viscosity of the aqueous gel containing the sulfonic polymer in the presence of the sodium salt of 3-hydroxy-2-pentylcyclopentaneacetic acid.

EXAMPLE 3

A skin care cream having the following composition was prepared:

|  | Example 3 |
|---|---|
| Sodium salt of 3-hydroxy-2-pentylcyclopentaneacetic acid at 30% in a water/dipropylene glycol mixture (70/30) | 13.4%, i.e. 4% AM |
| Crosslinked acrylic acid homopolymer (Carbopol Ultrez 10 from Lubrizol) | 0.25 |
| Polyacrylamidomethylpropanesulfonic acid partially neutralized with aqueous ammonia and highly crosslinked (HOSTACERIN AMPS ® from Clariant) | 0.5 |
| Hydroxyethylcellulose (Natrosol 250 HHR from Aqualon) | 0.25 |
| Sodium hyaluronate (Cristalhyal from Soliance) | 0.1 |
| Xanthan gum | 0.1 |
| Ethanol | 5 |
| Glycerol | 3 |
| Sodium hydroxide | 0.12 |
| Disodium salt of ethylenediaminetetraacetic acid | 0.1 |
| Preservative | qs |
| Water | qs 100 |
| centrifugation | Remains homogeneous |
| Microscopic appearance | Homogeneous |
| Stability 2 months at 25° C. and 45° C. | Stable |

The composition spreads pleasantly on the skin without any sensation of a tacky effect and without pilling.

COMPARATIVE EXAMPLES 4 TO 6

Three oil-in-water emulsions (skin care serum) containing the sodium salt of 3-hydroxy-2-pentylcyclopentane acid were prepared:
An emulsion (example 4) according to the invention comprising the combination of polyacrylamidomethylpropane sulfonic acid partially neutralized with aqueous ammonia and crosslinked (Hostacerin AMPS® from Clariant) (referred to as polymer B) and of the crosslinked acrylic acid homopolymer (Carbopol Ultrez 10 from Lubrizol) (referred to as polymer C);
An emulsion (example 5) outside the invention, similar to example 4, in which the amount of polymer C has been replaced with the same amount of polymer B;
An emulsion (example 6) outside the invention, similar to example 4, in which the amount of polymer B has been replaced with the same amount of polymer C.

For each composition, microscopic evaluation of the composition was carried out.

The following results were obtained:

|  | Example | | |
|---|---|---|---|
|  | 4 (invention) | 5 (outside the invention) | 6 (outside the invention) |
| Sodium salt of 3-hydroxy-2-pentylcyclopentaneacetic acid at 30% in a water/dipropylene glycol mixture (70/30) | 13.4%, i.e. 4% AM | 13.4%, i.e. 4% AM | 13.4%, i.e. 4% AM |
| Water | qs 100 | qs 100 | qs 100 |
| Crosslinked acrylic acid homopolymer (Carbopol Ultrez 10 from Lubrizol) (polymer C) | 0.4 | 0 | 1.2 |
| Polyacrylamidomethyl-propanesulfonic acid partially neutralized with aqueous ammonia and crosslinked (Hostacerin AMPS ® from Clariant) (polymer B) | 0.8 | 1.2 | 0 |
| Hydroxyethylcellulose (Natrosol 250 HHR from Aqualon) | 0.25 | 0.25 | 0.25 |
| Sodium hyaluronate (Cristalhyal from Soliance) | 0.1 | 0.1 | 0.1 |
| Glycerol | 8 | 8 | 8 |
| Ethanol | 5 | 5 | 5 |
| $C_{14}$-$C_{22}$ alcohol/$C_{12}$-$C_{20}$ alkylglucoside mixture (80/20) (Montanov 68 ® from SEPPIC) | 1 | 1 | 1 |
| Polydimethylsiloxane 10 cst | 2 | 2 | 2 |
| Limnanthes alba oil | 0.5 | 0.5 | 0.5 |
| Liquid petroleum jelly | 1 | 1 | 1 |
| Disodium salt of ethylenediaminetetraacetic acid | 0.1 | 0.1 | 0.1 |
| Sodium hydroxide | 0.2 | 0.07 | 0.46 |
| Adenosine | 0.1 | 0.1 | 0.1 |
| Preservative | qs | qs | qs |
| Microscopic appearance | Homogeneous | Nonhomogeneous | Nonhomogeneous |

These tests show that the formula according to the invention (ex 4) is stable, whereas the compositions comprising only polymer B (ex 5) or only polymer C (ex 6) are not stable.

Thus, the combination of polymers B and C makes it possible to stabilize the emulsion.

The serum applied to the skin spreads easily, while fluidizing, without any tacky sensation and without pilling.

What is claimed is:

1. A composition comprising, in a physiologically acceptable aqueous medium, a compound of formula (I) below:

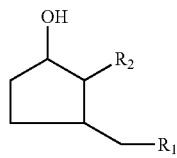

in which:

$R_1$ represents a radical $COOR_3$, $R_3$ denoting a hydrogen atom or a $C_1$-$C_4$ alkyl radical, optionally substituted with one or more hydroxyl groups;

$R_2$ represents a saturated or unsaturated linear hydrocarbon-based radical containing from 1 to 18 carbon atoms or a saturated or unsaturated branched or cyclic hydrocarbon-based radical containing from 3 to 18 carbon atoms;

and also the optical isomers thereof, and corresponding salts;

a homopolymer of a monomer comprising a sulfonic group;

and a crosslinked acrylic acid homopolymer.

2. The composition as claimed in claim 1, characterized in that the compound (I) is such that $R_1$ denotes a radical chosen from —COOH, —COOMe, —COO—$CH_2$—$CH_3$, —COO—$CH_2$—CH(OH)—$CH_2OH$, —$COOCH_2$—$CH_2$—$CH_2OH$, —$COOCH_2$—CH(OH)—$CH_3$;

$R_2$ denotes a saturated or unsaturated linear hydrocarbon-based radical containing from 2 to 6 carbon atoms.

3. The composition as claimed in claim 1, characterized in that the compound (I) is 3-hydroxy-2-pentylcyclopentaneacetic acid.

4. The composition as claimed in claim 1, characterized in that the compound of formula (I) is present in a content ranging from 1% to 10% by weight, relative to the total weight of the composition.

5. The composition as claimed in claim 1, characterized in that the monomer comprising a sulfonic group is 2-acrylamido-2-methylpropanesulfonic acid.

6. The composition as claimed in claim 1, characterized in that the homopolymer of a monomer comprising a sulfonic group is a crosslinked and neutralized homopolymer of 2-acrylamido-2-methylpropanesulfonic acid.

7. The composition as claimed in claim 1, characterized in that the homopolymer of a monomer comprising a sulfonic group is present in a content ranging from 0.05% to 5% by weight relative to the total weight of the composition.

8. The composition as claimed in claim 1, characterized in that the acrylic acid homopolymer is present in an amount ranging from 0.01% to 5% by weight, relative to the total weight of the composition.

9. The composition as claimed in claim 1, characterized in that it is in the form of an oil-in-water emulsion.

10. The composition as claimed in claim 9, characterized in that it comprises a surfactant of alkylpolyglycoside type.

11. The composition as claimed in claim 10, characterized in that said alkylpolyglycoside is a compound of formula (II):

$$R(O)(G)_x \quad \quad (II)$$

in which the radical R is a linear or branched $C_{12}$-$C_{22}$ alkyl radical, x ranges from 1 to 5 and G is a saccharide residue chosen from glucose, dextrose, saccharose, fructose, galactose, maltose, maltotriose, lactose, cellobiose, mannose, ribose, dextran, talose, allose, xylose, levoglucan, cellulose and starch.

12. The composition as claimed in claim 11, characterized in that G is a glucose residue.

13. The composition as claimed in claim 10, characterized in that the surfactant of alkylpolyglycoside type is present in a content ranging from 0.1% to 1.6% by weight, relative to the total weight of the composition.

14. The composition as claimed in claim 10, characterized in that it comprises a fatty alcohol comprising from 10 to 30 carbon atoms.

15. The composition as claimed in claim 14, characterized in that the fatty alcohol is present in a content ranging from 0.4% to 8% by weight, relative to the total weight of the composition.

16. The composition as claimed in claim 1, characterized in that it comprises an oil in a content ranging from 0.5% to 20% by weight, relative to the total weight of the composition.

17. The composition as claimed in claim 1, characterized in that it comprises a cosmetic additive chosen from emulsifiers, gelling agents, oils, waxes, preservatives, antioxidants, water, fragrances, fillers, UV screens, pigments, fibers, chelating agents, odor absorbers and colorants.

18. A non-therapeutic cosmetic treatment process for keratin materials, comprising the application to said keratin materials of a cosmetic composition as defined in claim 1.

19. The composition as claimed in claim 2, characterized in that the compound of formula (I) is present in a content ranging from 1% to 10% by weight, relative to the total weight of the composition.

20. The composition as claimed in claim 3, characterized in that the compound of formula (I) is present in a content ranging from 1% to 10% by weight, relative to the total weight of the composition.

* * * * *